(12) United States Patent
Mironer

(10) Patent No.: US 9,682,049 B2
(45) Date of Patent: Jun. 20, 2017

(54) NON-RACEMIC MIXTURES OF VARIOUS RATIOS OF D- AND L-METHADONE AND METHODS OF TREATING PAIN USING THE SAME

(71) Applicant: Y. Eugene Mironer, Spartanburg, SC (US)

(72) Inventor: Y. Eugene Mironer, Spartanburg, SC (US)

( * ) Notice: Subject to any disclaimer, the term of this patent is extended or adjusted under 35 U.S.C. 154(b) by 0 days.

(21) Appl. No.: 14/850,613

(22) Filed: Sep. 10, 2015

(65) Prior Publication Data

US 2016/0235691 A1    Aug. 18, 2016

Related U.S. Application Data

(60) Provisional application No. 62/176,430, filed on Feb. 18, 2015.

(51) Int. Cl.
*A61K 31/137* (2006.01)
*A61K 45/06* (2006.01)

(52) U.S. Cl.
CPC ............ *A61K 31/137* (2013.01); *A61K 45/06* (2013.01)

(58) Field of Classification Search
USPC ........................................................ 514/648
See application file for complete search history.

(56) References Cited

U.S. PATENT DOCUMENTS

| 2,983,757 A | 5/1961 | Zaugg |
| 6,897,242 B1 | 5/2005 | Somerville et al. |
| 2014/0088155 A1 | 3/2014 | Manfredi et al. |

OTHER PUBLICATIONS

Davis (d-Methadone Blocks Morphine Tolerance and N-Methyl-DAspartate-Induced Hyperalgesia, The Journal of Pharmacology and Experimental Therapeutics, vol. 289, No. 2, 1999, pp. 1048-1053).*
Maria Luisa Sotgiu et al., "Cooperative N-methyl-$_D$-aspartate (NMDA) receptor antagonism and μ-opioid Receptor Agonism Mediate the Methadone Inhibition of the Spinal Neuron Pain-Related Hyperactivity in a Rat Model of Neuropathic Pain", Pharmacological Research, (2009), vol. 60, pp. 284-290.
Li He et al., "An Opiate Cocktail that Reduces Morphine Tolerance and Dependence", Current Biology, 2005, vol. 15, pp. 1028-1033.
Richard W. Morgan et al., "Characterization of the Antinociceptive Effects of the Individual Isomers of Methadone Following Acute and Chronic Administration", Behav Pharmacol., 2011, (thirteen (13) pages).
Elizabeth A. Bolan et al., "Synergy Between μ Opioid Ligands: Evidence for Functional Interactions Among μ Opioid Receptor Subtypes", The Journal of Pharmacology and Experimental Therapeutics, 2002, vol. 303, No. 2, pp. 557-562.
Carpenter KJ et al., "Neuronal Inhibitory Effects of Methadone are Predominately Opioid Receptor Mediated in the Rat Spinal Cord in Vivo", Palliative.org, 2008, (four (4) pages).
Boris A. Chizh et al., "The N-methyl-$_D$-Aspartate Antagonistic and Opioid Components of d-methadone Antinociception in the Rat Spinal Cord", Neuroscience Letters, (2000), vol. 296, pp. 117-120.
Kim Lemberg, DDS et al., "Morphine, Oxycodone, Methadone and Its Enantiomers in Different Models of Nociception in the Rat", Anesth Analg, 2006, vol. 102, pp. 1768-1774.
John S. Morley et al., "Low-dose Methadone has an Analgesic Effect in Neuropathic Pain: a Double-Blind Randomized Controlled Crossover Trial", Palliative Medicine, 2003, pp. 576-587.
Naohito Shimoyama et al., "d-Methadone Is Antinociceptive in the Rat Formalin Test[1]", The Journal of Pharmacology and Experimental Therapeutics, 1997, vol. 283, No. 2, pp. 648-652.
Moryl N et al., "Pitfalls of Opioid Rotation: Substituting Another Opioid for Methadone in Patients with Cancer Pain", Palliative.org, 2002, (three (3)pages).
Dinah Gould et al., "Examining the Validity of Pressure Ulcer Risk Assessment Scales: Developing and Using Illustrated Patient Simulations to Collect the Data", Journal of Clinical Nursing, 2001, vol. 10, pp. 697-706.

* cited by examiner

*Primary Examiner* — Kathrien Cruz
(74) *Attorney, Agent, or Firm* — Crowell & Moring LLP

(57) ABSTRACT

Non-racemic mixtures of D- and L-methadone containing a ratio ranging from about 2.5:1 to about 3.5:1 by weight of D-methadone to L-methadone, such as for example about 2.9:1 to about 3.1:1 by weight of D-methadone to L-methadone, or about 3:1 by weight of D-methadone to L-methadone, have been found to exhibit surprising and unexpected beneficial results in the treatment of neuropathic pain. Additionally, non-racemic mixtures of D- and L-methadone containing a ratio ranging from about 2.5:1 to about 3.5:1 by weight of D-methadone to L-methadone, about 2.9:1 to about 3.1:1 by weight of D-methadone to L-methadone, or for example about 3:1 by weight of D-methadone to L-methadone, in combination with other non-methadone opioids have been found to exhibit surprising and unexpected beneficial results in the treatment of mixed pain.

9 Claims, No Drawings

NON-RACEMIC MIXTURES OF VARIOUS RATIOS OF D- AND L-METHADONE AND METHODS OF TREATING PAIN USING THE SAME

CROSS-REFERENCE TO RELATED APPLICATION

The present application claims the benefit under 35 U.S.C. §119 of previously filed U.S. Provisional Application No. 62/176,430, filed Feb. 18, 2015, the entirety of which is herein incorporated by reference.

BRIEF DESCRIPTION

Non-racemic mixtures of D- and L-methadone containing a ratio ranging from about 2.5:1 to about 3.5:1 by weight of D-methadone to L-methadone, such as for example about 2.9:1 to about 3.1:1 by weight of D-methadone to L-methadone or about 3:1 by weight of D-methadone to L-methadone, have been found to exhibit surprising and unexpected beneficial results in the treatment of neuropathic pain. Additionally, non-racemic mixtures of D- and L-methadone containing a ratio ranging from about 2.5:1 to about 3.5:1 by weight of D-methadone to L-methadone, such as for example about 2.9:1 to about 3.1:1 by weight of D-methadone to L-methadone or about 3:1 by weight of D-methadone to L-methadone, in combination with other non-methadone opioids have been found to exhibit surprising and unexpected beneficial results in the treatment of mixed pain. Combination of non-racemic mixtures of D- and L-methadone with opioids are also helpful in reducing side effects, including providing a reduction in the development of tolerance to opioids.

BACKGROUND OF THE INVENTION

Methadone is a well-known, synthetic opioid that is widely used in alleviating chronic pain as well as in treatment of opioid addiction. Methadone, as commonly used, is a racemic mixture of D- and L-isomers. See e.g., Shimoyama et al., *JPET,* 283:648-652 (1997).

It is well-established that the L-isomer of methadone has µ-opioid activity as well as N-methyl-D-aspartate (NMDA) receptor antagonist activity. The L-isomer also possesses the ability to block re-uptake of noradrenaline and serotonin. Unlike the L-isomer, the D-isomer of methadone has weak µ-opioid activity but has NMDA receptor antagonist activity.

Shimoyama et al., 283(2): 648-52 (1997) showed that intrathecal D-methadone produced antinociception in a neuropathic pain model in rats where antinociception was not reversed by naloxone. Naloxone acts as an opioid antagonist and can be used to counter the effects of opioids by binding opioid receptors including the µ-opioid receptor. Failure of naloxone to reverse antinociception caused by D-methadone suggested that D-methadone has an NMDA-receptor antagonism mechanism of action rather than an opioid-receptor method of action. U.S. Pat. No. 6,008,258 relates to treatment of neuropathic pain with the D-isomer of methadone.

However, more recent studies question the mechanism and efficacy of D-methadone. Carpenter et al., *European Journal of Pain* 4(1): 19-26 (2000) showed that racemic methadone inhibited C-fiber evoked response similar to morphine. D-methadone showed weaker but similar inhibitory activity that was blocked by naloxone.

Chizh et al., *Neurosci. Ltrs* 296: 117-20 (2000) showed that antinociceptive activity of D-methadone in different pain models was blocked by naloxone, making NMDA antagonism an unlikely contributor to its mechanism of action. Lemberg et al., *Anesthesia & Analgesia* 102: 1768-74 (2006) revealed that in neuropathic pain L-methadone showed greater potency than other opioids, while D-methadone was inactive. Finally, Sotgiu et al., *Pharm. Res.* 60: 284-90 (2009) demonstrated that in a neuropathic pain model, naloxone blocked the majority of, but not all, nociception by a racemic mixture of methadone, suggesting involvement of both the µ-opioid receptor and NMDA receptor antagonism.

Methadone efficacy has been tested in a double-blind randomized controlled study by Morley et al., *Palliative Med.* 17(7):576-87 (2003). This study showed an analgesic effect of racemic methadone in neuropathic pain. By contrast, a small group of patients with neuropathic pain enrolled in a phase I study of D-methadone showed no analgesic response despite a high dose of D-methadone, as discussed in U.S. Patent Application No. 2014/0088155.

U.S. Pat. No. 6,897,242 provides for the use of a non-racemic methadone mixture for treatment of chronic pain.

The varying efficacy in treatment of pain reported for different methadone isomers and different types of pain as well as the prevalence of neuropathic pain reveal a need to attain more effective dosing of methadone isomers in order to best treat pain, such as for example neuropathic pain and mixed pain.

Back pain alone has a neuropathic component in 41-55% of cases, with more than 2 million cases of neuropathic back pain the United States. Currently available options for treatment of neuropathic back pain, such as for example tapentadol, D-methadone with another opioid, or racemic methadone, are inadequate and pose risks of side effects as well as risks of tolerance and addiction.

Drug compositions that increase safety and decrease risk of tolerance and side effects are desirable for the pain, such as neuropathic pain. The non-racemic mixtures of the D- and L-forms of methadone disclosed herein, compositions comprising such mixtures and methods of treatment using such mixtures and compositions unexpectedly provide such advantages.

SUMMARY OF THE INVENTION

The present invention includes and provides mixtures comprising about 2.5:1 to about 3.5:1 by weight of D-methadone or pharmaceutically acceptable salt thereof to L-methadone or pharmaceutically acceptable salt thereof. The present invention includes and provides mixtures containing about 2.9:1 to about 3.1:1 by weight of D-methadone or pharmaceutically acceptable salt thereof to L-methadone or pharmaceutically acceptable salt thereof. The present invention also includes and provides mixtures containing about 3:1 by weight of D-methadone or pharmaceutically acceptable salt thereof to L-methadone or pharmaceutically acceptable salt thereof.

The present invention further includes and provides mixtures containing any ratio range that falls within the range of about 2.5:1 to about 3.5:1 by weight of D-methadone or pharmaceutically acceptable salt thereof to L-methadone or pharmaceutically acceptable salt thereof.

The present invention also includes and provides pharmaceutical compositions comprising the non-racemic mixtures described herein and methods of treatment using such non-racemic mixtures and compositions.

The non-racemic mixtures described herein, compositions comprising such mixtures and methods of treatment using such mixtures or compositions comprising such mixtures show surprising and unexpected results in the treatment of neuropathic pain or mixed pain. Further, the non-racemic mixtures, compositions and methods of treatment of the present invention unexpectedly result in reduced side effects in subjects who are treated.

The present invention includes and provides non-racemic mixtures comprising about 2.5:1 to about 3.5:1 by weight of D-methadone or pharmaceutically acceptable salt thereof to L-methadone or pharmaceutically acceptable salt thereof and at least one non-methadone opioid that show surprising and unexpected effects, for example in the treatment of mixed pain. The present invention includes and provides non-racemic mixtures comprising about 2.9:1 to about 3.1:1 by weight of D-methadone or pharmaceutically acceptable salt thereof to L-methadone or pharmaceutically acceptable salt thereof and at least one non-methadone opioid that show surprising and unexpected effects, for example in the treatment of mixed pain. The present invention also includes and provides non-racemic mixtures comprising about 3:1 by weight of D-methadone or pharmaceutically acceptable salt thereof and L-methadone or pharmaceutically acceptable salt thereof and at least one non-methadone opioid that show surprising and unexpected effects, for example in the treatment of mixed pain.

For example, the present invention includes and provides a composition comprising a non-racemic mixture of D-methadone or a pharmaceutically acceptable salt thereof and L-methadone or pharmaceutically acceptable salt thereof and a pharmaceutically acceptable carrier, wherein the D-methadone or pharmaceutically acceptable salt thereof and L-methadone or pharmaceutically acceptable salt thereof are present in a ratio range from about 2.5:1 to about 3.5:1 by weight. The present invention includes and provides a composition comprising a non-racemic mixture of D-methadone or a pharmaceutically acceptable salt thereof and L-methadone or pharmaceutically acceptable salt thereof and a pharmaceutically acceptable carrier, wherein the D-methadone or pharmaceutically acceptable salt thereof and L-methadone or pharmaceutically acceptable salt thereof are present in a ratio range from about 2.9:1 to about 3.1:1 by weight. The present invention also includes and provides a composition comprising a non-racemic mixture of D-methadone or a pharmaceutically acceptable salt thereof and L-methadone or pharmaceutically acceptable salt thereof and a pharmaceutically acceptable carrier, wherein the D-methadone or pharmaceutically acceptable salt thereof and L-methadone or pharmaceutically acceptable salt thereof are present in a ratio of about 3:1 by weight.

The present invention includes and provides a composition comprising a non-racemic mixture of D-methadone or a pharmaceutically acceptable salt thereof and L-methadone or pharmaceutically acceptable salt thereof, at least one non-methadone opioid, and a pharmaceutically acceptable carrier, wherein the D-methadone or pharmaceutically acceptable salt thereof and L-methadone or pharmaceutically acceptable salt thereof are present in a ratio range from about 2.5:1 to about 3.5:1 by weight. The present invention includes and provides a composition comprising a non-racemic mixture of D-methadone or a pharmaceutically acceptable salt thereof and L-methadone or pharmaceutically acceptable salt thereof, at least one non-methadone opioid, and a pharmaceutically acceptable carrier, wherein the D-methadone or pharmaceutically acceptable salt thereof and L-methadone or pharmaceutically acceptable salt thereof are present in a ratio range from about 2.9:1 to about 3.1:1 by weight. The present invention also includes and provides a composition comprising a non-racemic mixture of D-methadone or a pharmaceutically acceptable salt thereof and L-methadone or pharmaceutically acceptable salt thereof, at least one non-methadone opioid, and a pharmaceutically acceptable carrier, wherein the D-methadone or pharmaceutically acceptable salt thereof and L-methadone or pharmaceutically acceptable salt thereof are present in a ratio of about 3:1 by weight.

The present invention includes and provides a method for treatment of neuropathic pain in a subject comprising administering a composition comprising a non-racemic mixture of D-methadone or a pharmaceutically acceptable salt thereof and L-methadone or pharmaceutically acceptable salt thereof and a pharmaceutically acceptable carrier, wherein the D-methadone or pharmaceutically acceptable salt thereof and L-methadone or pharmaceutically acceptable salt thereof are present in a ratio range from about 2.5:1 to about 3.5:1 by weight. The present invention further includes and provides a method for treatment of neuropathic pain in a subject comprising administering a composition comprising a non-racemic mixture of D-methadone or a pharmaceutically acceptable salt thereof and L-methadone or pharmaceutically acceptable salt thereof and a pharmaceutically acceptable carrier, wherein the D-methadone or pharmaceutically acceptable salt thereof and L-methadone or pharmaceutically acceptable salt thereof are present in a ratio range from about 2.9:1 to about 3.1:1 by weight. The present invention also includes and provides a method for treatment of neuropathic pain in a subject comprising administering a composition comprising a non-racemic mixture of D-methadone or a pharmaceutically acceptable salt thereof and L-methadone or pharmaceutically acceptable salt thereof and a pharmaceutically acceptable carrier, wherein the D-methadone or pharmaceutically acceptable salt thereof and L-methadone or pharmaceutically acceptable salt thereof are present in a ratio of about 3:1 by weight.

The present invention further includes and provides a method for treatment of mixed pain in a subject comprising administering a composition comprising a non-racemic mixture of D-methadone or a pharmaceutically acceptable salt thereof and L-methadone or pharmaceutically acceptable salt thereof, at least one non-methadone opioid, and a pharmaceutically acceptable carrier, wherein the D-methadone or pharmaceutically acceptable salt thereof and L-methadone or pharmaceutically acceptable salt thereof are present in a ratio range from about 2.5:1 to about 3.5:1 by weight. The present invention includes and provides a method for treatment of mixed pain in a subject comprising administering a composition comprising a non-racemic mixture of D-methadone or a pharmaceutically acceptable salt thereof and L-methadone or pharmaceutically acceptable salt thereof, at least one non-methadone opioid, and a pharmaceutically acceptable carrier, wherein the D-methadone or pharmaceutically acceptable salt thereof and L-methadone or pharmaceutically acceptable salt thereof are present in a ratio range from about 2.9:1 to about 3.1:1 by weight. The present invention also includes and provides a method for treatment of mixed pain in a subject comprising administering a composition comprising a non-racemic mixture of D-methadone or a pharmaceutically acceptable salt thereof and L-methadone or pharmaceutically acceptable salt thereof, at least one non-methadone opioid, and a pharmaceutically acceptable carrier, wherein the D-methadone or pharmaceutically acceptable salt thereof and L-methadone or pharmaceutically acceptable salt thereof are present in a ratio of about 3:1 by weight.

DETAILED DESCRIPTION OF THE INVENTION

By the present invention, a composition is provided which comprises a non-racemic mixture of D-methadone or pharmaceutically acceptable salt thereof and L-methadone or pharmaceutically acceptable salt thereof in a ratio of about 2.5:1 to about 3.5:1, about 2.9:1 to about 3.1:1, or preferably a ratio of about 3:1 by weight of D-methadone to L-methadone.

As described herein, a non-racemic mixture of the present invention includes any mixture where D-methadone or pharmaceutically acceptable salt thereof and L-methadone or pharmaceutically acceptable salt thereof are present in a ratio range of about 2.5:1 to about 3.5:1, about 2.9:1 to 3.1:1 or preferably a ratio of about 3:1 by weight.

Ratios of D-methadone to L-methadone provided herein are provided as weight ratios, which also equate to molecular ratios of 100% pure enantiomers.

Optical resolution of methadone may be accomplished by any of several methods well-known in the art. For example, by the use of D-tartaric acid, D-methadone and L-methadone, or their hydrochlorides, are resolved by forming a readily purifiable, water-insoluble d-α-bromocamphor-n-sulfonate of the D-isomer. D-methadone is then precipitated by slow addition of water. The L-form is obtained from the mother liquor by forming the D-tartrate salt.

A method for simultaneous resolution of both optical isomers of methadone is taught in U.S. Pat. No. 2,983,757. The method is based on the knowledge that a seed crystal of the dextro-rotatory isomer will attract the D-isomer in saturated solution, and when the degree of saturation of the solute in the solution is increased, the D-isomer will tend to crystallize out on the D-isomer seed crystal. At the same time, a portion of the L-isomer will tend to crystallize out on the L-isomer seed crystal. This process will continue so long as the solution is supersaturated with the composition or solute and seeded crystals will grow to substantial size. At conclusion, crystals of the D-isomer and L-isomer will have been grown on the seed crystals.

A non-racemic mixture as detailed herein comprises more D-methadone than L-methadone, where the ratio of D-methadone to L-methadone or pharmaceutically acceptable salts thereof may be about 2.5:1, about 2.6:1, about 2.7:1, about 2.8:1, about 2.9:1, about 3.0:1, about 3.1:1, about 3.2:1, about 3.3:1, about 3.4:1, or about 3.5:1 by weight.

In addition to being in the range from about 2.5:1 to about 3.5:1, the ratio of D-methadone or pharmaceutically acceptable salt thereof to L-methadone or pharmaceutically acceptable salt thereof may be in any ratio range within that range. By way of non-limiting example, the ratio of D-methadone to L-methadone may be in a range from about 2.6:1 to about 3.4:1, from about 2.7:1 to about 3.3:1, from about 2.8:1 to about 3.2:1, from about 2.9:1 to about 3.1:1, from about 2.5:1 to about 3.0:1, from about 2.6:1 to about 3.0:1, from about 2.7:1 to about 3.0:1, from about 2.8:1 to about 3.0:1, from about 2.9:1 to about 3.0:1, from about 3.0:1 to about 3.5:1, from about 3.1:1 to about 3.4:1, or from about 3.2:1 to about 3.3:1 by weight.

When using a combination of D-methadone and L-methadone, it is envisioned that a pharmaceutically acceptable salt of either D-methadone or L-methadone may optionally be substituted for either methadone enantiomer. Alternatively, both D-methadone and L-methadone may be substituted by corresponding pharmaceutically acceptable salts. It is also contemplated that pharmaceutically acceptable salts of non-methadone opioids may also be substituted for non-methadone opioids.

Generally, as used herein, a salt refers to a compound prepared by the reaction of an organic acid or base drug with a pharmaceutically acceptable mineral or organic acid or base; as used herein, salt may include hydrates and solvates of salts made in accordance with this invention. Exemplary pharmaceutically acceptable mineral or organic acids or bases are as listed for example in Tables 1-8 in *Handbook of Pharmaceutical Salts*, P. H. Stahl and C. G. Wermuth (eds.), VHCA, Zurich, pp. 334-345 (2002).

A mixture or composition comprising D-methadone or pharmaceutically acceptable salt thereof and L-methadone or pharmaceutically acceptable salt thereof in the ratios provided herein is acceptable for administration to a subject. In an embodiment, the mixture or composition is acceptable for administration to a mammal, and in a preferred embodiment to a human.

Examples of pharmaceutically acceptable salts of acids include without limitation salts of hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, saccharic acid, monomethylsebacic acid, 5-oxo-proline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and aspartic acid.

Examples of pharmaceutically acceptable salts of bases include without limitation the salts of alkali metals, alkaline earth metals, and ammonium salts.

Dosages of a pharmaceutical composition of the invention will vary widely based on a number of factors, including for example patient pain level, pain type, pain tolerance, source of pain, age, height, and weight. Dosages of a non-racemic methadone composition as discussed herein are dosages of D-methadone and L-methadone combinations (in the ratios as discussed herein) and do not include additional pharmaceutically active ingredients, which may be used as discussed herein in additional dosages.

The actual dosages of a non-racemic methadone composition in a ratio as described herein can vary widely from about 3 mg/day to about 300 mg/day. Dosage of a pharmaceutical composition comprising methadone in a ratio as provided herein may be for example about 5 mg/day to about 50 mg/day, about 10 mg/day to about 250 mg/day, about 10 mg/day to about 100 mg/day, about 50 mg/day to about 100 mg/day, about 50 mg/day to about 150 mg/day, about 50 mg/day to about 200 mg/day, about 50 mg/day to about 250 mg/day, about 75 mg/day to about 250 mg/day, about 100 mg/day to about 150 mg/day, about 100 mg/day to about 200 mg/day, about 150 mg/day to about 200 mg/day, about 150 mg/day to about 250 mg/day, about 150 mg/day to about 300 mg/day, about 200 mg/day to about 250 mg/day, about 200 mg/day to about 300 mg/day, or about 250 mg/day to about 300 mg/day.

Dosage of a pharmaceutical composition comprising methadone in a ratio as described herein may be about 3 mg/day, about 4 mg/day, about 5 mg/day, about 10 mg/day, about 15 mg/day, about 20 mg/day, about 25 mg/day, about 50 mg/day, about 75 mg/day, about 100 mg/day, about 125 mg/day, about 150 mg/day, about 175 mg/day, about 200 mg/day, about 225 mg/day, about 250 mg/day, about 275 mg/day, or about 300 mg/day. Depending on the frequency of administration, each dosage unit may contain from about 1 mg to about 100 mg per unit dose.

In addition to D-methadone or pharmaceutically acceptable salt thereof and L-methadone or pharmaceutically acceptable salt thereof, the mixtures and compositions of the present invention may further comprise other pharmaceutically active ingredients such as for example, non-methadone opioids, partial opioid agonists, non-opioid analgesics, skeletal muscle relaxants, nonbarbituate sedatives, and other such pharmaceutically active components.

Where one or more of such other pharmaceutically active ingredients are included, the D-methadone or pharmaceutically acceptable salt thereof and L-methadone or pharmaceutically acceptable salt thereof remain in the ratios or ratio ranges described herein. These other pharmaceutically active ingredients may be added in the smallest dose of active ingredient to achieve satisfactory pain therapy or other desired pharmacological effect. To the extent possible, such other ingredients should be administered to maximize therapeutic effect without the occurrence of intolerable side effects.

In general, the other pharmaceutically active ingredients may be administered in amounts up to their maximum daily dose, which is known to those skilled in the art. Indeed, recommended doses of these other ingredients are well known to the skilled artisan and may be found in the literature, including for example in the Physician's Desk Reference, PDR Network, 68$^{th}$ edition (2014). By way of non-limiting example, acetylsalicylic acid may preferably be administered in a maximum daily dose up to 4,000 mg.

In some instances, co-administration of another ingredient with mixtures and compositions comprising D-methadone or pharmaceutically acceptable salt thereof and L-methadone or pharmaceutically acceptable salt thereof in the ratios described herein will allow the other ingredient to be administered in a lesser amount than when the other pharmaceutically active ingredient is administered alone. For example, the dosage of the other pharmaceutically active ingredient may be lowered while still achieving satisfactory pain therapy or other desired pharmacological effect. Also, the administration of the other pharmaceutically active ingredient and the compositions comprising D-methadone or pharmaceutically acceptable salt thereof and L-methadone or pharmaceutically acceptable salt thereof in the ratios described herein may result in a more than additive, unexpectedly improved therapeutic effect.

The lesser amount of the other pharmaceutically active ingredient will preferably be an amount that is equieffective to its activity in the absence of D-methadone or pharmaceutically acceptable salt thereof and L-methadone or pharmaceutically acceptable salt thereof. In this regard, "equieffective" refers to the dosage of the other pharmaceutically active ingredient that would be required in order to achieve the equivalent desired therapeutic effect as when the other ingredient is administered alone. This lesser amount can be calculated by the skilled artisan based on measurement of $ED_{50}$ values of the other pharmaceutically active ingredient with and without co-administration of D-methadone or pharmaceutically acceptable salt thereof and L-methadone or pharmaceutically acceptable salt thereof in ratios according to the present invention.

Interaction studies may be performed in order to determine the requisite dosage of the other pharmaceutically active ingredient by comparing the theoretically additive effect of a defined dosage of the other pharmaceutically active ingredient with the experimentally determined effect of the other pharmaceutically active ingredient when combined with D-methadone or pharmaceutically acceptable salt thereof and L-methadone or pharmaceutically acceptable salt thereof in a ratio of the present invention.

Efficacy calculation should be measured at the time point of peak effect of the other pharmaceutically active ingredient. Where the other pharmaceutically active ingredient shows higher experimental determined efficacy than the theoretically-calculated efficacy, an unexpected result is apparent and dosage of the other pharmaceutically active ingredient may be reduced.

A non-racemic methadone mixture or composition of the present invention may further comprise a non-methadone opioid drug or pharmaceutically acceptable salt thereof. A non-methadone opioid drug or pharmaceutically acceptable salt thereof may be present in a pharmacologically effective amount. In the context of the present invention, a pharmacologically effective amount refers to an amount of drug used to produce a desired pharmacological effect in a subject. A pharmacologically effective amount may be anticipated on the basis of in vitro testing or clinical testing. A pharmacologically effective amount may also be discerned based on judgment of a clinician regarding the experience of a particular subject.

A non-methadone opioid drug of the present invention also includes opiates as well as opioids. A non-methadone opioid drug of the present invention may be naturally extracted. Alternatively, a non-methadone opioid drug of the present invention may be synthetically synthesized in whole or in part.

Non-methadone opioid drugs include, for example without limitation, tramadol, tapentadol, hydrocodone, oxycodone, morphine, codeine, diphenoxylate, fentanyl, hydromorphine, meperidine, dihydroetorphine, ethylmorphine, etorphine hydrochloride, metopon, oripavine, oxymorphone, thebaine, alfentanil, alphaprodine, anileridine, bezitramide, carfentanil, dihydrocodeine, levomorphan, levorphanol, metazocine, phenazocine, piminodine, racemethorphan, racemorphan, remifentanil, and sufentanil.

A non-racemic methadone mixture or composition of the present invention may comprise a partial opioid agonist. A partial opioid agonist may be present in a pharmacologically effective amount. Exemplary non-limiting partial opioid agonists include buprenorphine, pentazocine and butorphanol.

A composition of the present invention may optionally include one or more analgesic of the non-opioid type or a pharmaceutically acceptable salt thereof. Useful non-opioid analgesics include the coal-tar analgesics, in particular, acetaminophen, and nonsteroidal anti-inflammatory drugs (NSAIDs) such as aspirin, diclofenac, diflusinal, etodolac, fenbufen, fenoprofen, flufenisal, flurbiprofen, ibuprofen, indomethacin, ketoprofen, ketorolac, meclofenamic acid, mefanamic acid, nabumetone, naproxen, oxaprozin, phenylbutazone, piroxicam, sulindac, tolmetin, and zomepirac.

A composition of the present invention may also optionally include one or more skeletal muscle relaxant or pharmaceutically acceptable salt thereof. A skeletal muscle relaxant may be amobarbital, aprobarbital, butabarbital, mephobarbital, metharbital, methohexital, pentobarbital, phenobarbital, secobarbital, talbutal, theamylal, and thiopental. Other exemplary non-limiting skeletal muscle relaxants may include baclofen, carisoprodol, chlorzoxazone, cyclobenzaprine, methocarbamol, and orphrenadine.

A composition of the present invention may also optionally include a nonbarbiturate sedative or pharmaceutically acceptable salt thereof such as for example benzodiazepines (e.g., chlordiazepoxide, clorazepate, diazepam, flurazepam, lorazepam, oxazepam, temazepam, triazolam), $H_1$ antagonists (e.g., diphenhydramine, pyrilamine, promethazine, chlorpheniramine, chlorcyclizine), neuroleptics (e.g., droperidol) and other sedatives (e.g., glutethimide, meprobamate, methaqualone, dichloralphenazone).

A composition of the present invention may also optionally contain one or more other pharmacologically active components, including for example a stimulant (e.g., caffeine), an antihistamine (e.g., chlorpheniramine maleate), a decongestant (e.g., phenylephrine hydrochloride or phenylpropanolamine hydrochloride), a sympathomimetic (e.g., isometheptene mucate), or an anticonvulsant (e.g., gabapentin, phenyloin, carbamazepine, valproate, or clonazepam).

A methadone mixture or composition of the present invention may be administered in any form known to the skilled artisan. See e.g., Remington: The Science and Practice of Pharmacy, 19$^{th}$ edition, Mack Pub. Co., Easton, Pa. (1995). For example, administration may be oral (including immediate release, extended release, and continuous release forms); nasal; parenteral (for example, intravenous, intramuscular, subcutaneous, intraventricular, intrathecal, epidural, intracerebroventricular); transcutaneous, sublingual, or transbuccal injection. A mixture or composition of the present invention may be administered by means of a transdermal device such as a patch. Any other means of delivery known to the skilled artisan may be used, it being specifically understood that the foregoing list is not all inclusive.

A composition of the present invention can be formulated as a liquid (including an injectable solution, injectable suspension or oral liquid), powder, or elixir. Formulations for oral use can be provided as tablets, caplets or hard capsules wherein the pharmacologically active ingredients are mixed with an inert solid diluent such as calcium carbonate, sodium carbonate, calcium phosphate, lactose, talc, or kaolin, or as soft gelatin capsules wherein the active ingredients are mixed with an oleaginous medium, e.g., liquid paraffin or olive oil. Inert diluents and carriers which may be used in capsules include, for example, calcium carbonate, calcium phosphate, and kaolin.

A pharmaceutical composition of the present invention may be formulated with one or more pharmaceutically acceptable ingredients such as excipients. Any excipients known to the skilled artisan may be used in the pharmaceutical compositions of the present invention as will be appreciated by the skilled artisan. The following excipients are merely exemplary and may be substituted by other excipients known to the skilled art worker. Further exemplary excipients may be found for example in the Handbook of Pharmaceutical Excipients, (Raymond C. Rowe et al., eds.), 5$^{th}$ edit., APhA, London (2006).

A non-limiting example of excipients includes anti-adherents such as for example magnesium stearate to reduce adhesion or prevent sticking or both, binders such as for example saccharides and their derivatives (e.g., disaccharides such as sucrose and lactose, polysaccharides and their derivatives such as starches, cellulose, modified cellulose including for example microcrystalline cellulose and cellulose ethers such as for example hydroxylpropyl cellulose (HPC)), sugar alcohols (e.g., xylitol, sorbitol, maltitol), protein (e.g., gelatin), and synthetic polymers (e.g., polyvinylpyrrolidone (PVP) and polyethylene glycol (PEG)).

Another non-limiting example of excipients that may be included in the compositions of the present invention includes coatings such as for example cellulose (e.g., hydroxyproply methylcellulose (HPMC), synthetic polymers, shellac, corn protein zein or other polysaccharides), gelatin, fatty acids, waxes shellac, plastics and plant fibers. A coating may be used in a tablet, capsule. Tablets may also be uncoated. A coating may be enteric or non-enteric.

Other non-limiting excipients that may be included in the compositions of the present invention are colorings (e.g., titanium oxide and azo dyes), disintegrants (e.g., crosslinked polymers such as crosslinked polyvinylpyrrolidone, crosslinked sodium carboxymethyl cellulose, modified starch such as sodium starch glycolate, gelatin or acacia), flavorings (e.g., fruit extracts or artificial flavorings), glidants (e.g., fumed silica, talc, or magnesium carbonate), lubricants (e.g., talc, silica, fats such as vegetable stearin, magnesium stearate or stearic acid), preservatives (e.g., antioxidants such as vitamin A, vitamin E, vitamin C, retinyl palmitate, or selenium, amino acids such as cysteine or methionine, citric acid, sodium citrate, or synthetic preservatives such as methyl paraben or propyl paraben), sorbents (e.g., dessicants), sweeteners (e.g., sugar), or vehicles (e.g., petroleum or mineral oil).

The present invention also includes methods for treatment of pain in a subject comprising administering any of the non-racemic methadone mixtures or compositions in the ratios provided herein. By way of non-limiting example, the present invention includes a method for treatment of neuropathic pain in a subject comprising administering a mixture or composition of the present invention. The present invention includes a method for treatment of neuropathic pain in a subject comprising administering any mixture or composition of the present invention in the ratios described herein, wherein neuropathic pain is reduced or eliminated.

Administration of a mixture or composition of the present invention may continue for as long as desired to treat a subject. Duration of administration to a subject may be determined for example by a clinician. In determining over what period of time a mixture or composition of the present invention will be administered, a clinician may consider factors such as for example a subject's response to treatment, emergence of side effects, development of tolerance and the like.

The present invention includes a method for treatment of neuropathic pain in a subject comprising administering a non-racemic mixture comprising from about 2.5:1 to about 3.5:1 by weight of D-methadone or a pharmaceutically acceptable salt thereof to L-methadone or a pharmaceutically acceptable salt thereof, and a pharmaceutically acceptable carrier. The present invention also includes a method for treatment of neuropathic pain in a subject comprising administering a non-racemic mixture comprising from about 2.9:1 to about 3.1:1 by weight of D-methadone or a pharmaceutically acceptable salt thereof to L-methadone or a pharmaceutically acceptable salt thereof, and a pharmaceutically acceptable carrier. The present invention also includes a method for treatment of neuropathic pain in a subject comprising administering from about 3:1 by weight of D-methadone or a pharmaceutically acceptable salt thereof and L-methadone or a pharmaceutically acceptable salt thereof, and a pharmaceutically acceptable carrier.

The present invention also includes a method for treatment of mixed pain in a subject comprising any of the non-racemic methadone mixtures or compositions in the ratios provided herein and a non-methadone opioid. The present invention includes a method for treatment of mixed pain in a subject comprising administering any mixture or composition of the present invention in the ratios described herein and a non-methadone opioid, wherein the mixed pain is reduced or eliminated.

The present invention includes a method for treatment of mixed pain in a subject comprising administering a non-racemic mixture comprising from about 2.5:1 to about 3.5:1 by weight of D-methadone or a pharmaceutically acceptable salt thereof to L-methadone or a pharmaceutically acceptable salt thereof, at least one non-methadone opioid and a pharmaceutically acceptable carrier. The present invention also includes a method for treatment of mixed pain in a subject comprising administering a non-racemic mixture comprising from about 2.9:1 to about 3.1:1 by weight of D-methadone or a pharmaceutically acceptable salt thereof to L-methadone or a pharmaceutically acceptable salt thereof, at least one non-methadone opioid and a pharmaceutically acceptable carrier. The present invention also includes a method for treatment of mixed pain in a subject comprising administering a non-racemic mixture comprising about 3:1 by weight of D-methadone or a pharmaceutically acceptable salt thereof to L-methadone or a pharmaceutically acceptable salt thereof, and a pharmaceutically acceptable carrier.

Methods of treatment of pain as provided herein may also include administering any one or more of a non-methadone opioid, an opioid agonist, a partial opioid agonist, a non-opioid analgesic or any other pharmaceutically effective agent known to a skilled artisan, where a pharmaceutically effective agent includes any drug agent used to bring about an effect in a subject. Such non-methadone opioids, opioid agonists, partial opioid agonists, non-opioid analgesics or other pharmaceutically effective agents may be administered as part of the same dosage unit as the non-racemic methadone mixture or may be administered as a separate dosage form. Such non-methadone opioids, opioid agonists, partial opioid agonists, non-opioid analgesics or other pharmaceutically effective agents may be administered either before or after a non-racemic methadone mixture or composition or at the same time as a non-racemic methadone mixture or composition.

In the context of the present invention, a subject may include any animal and is preferably a mammal, and in a particularly preferred embodiment a human.

Pain that is treated may be any type of pain, including neuropathic pain, which is for example caused by damage or disease that affects the nervous system. Pain that is treated may be nociceptive pain, such as for example that caused by tissue damage or injury, including for example broken bones and cuts or scrapes. Pain may also be mixed such that it includes both neuropathic and nociceptive pain. In a preferred embodiment, pain that is treated is neuropathic. In another preferred embodiment, pain that is treated is mixed.

Pain treated by administration of the mixtures and compositions of the present invention may be acute or chronic. In a preferred embodiment, pain that is treated is chronic. In another preferred embodiment, pain that is treated is chronic, neuropathic pain.

Neuropathic pain may be found in conditions such as for example without limitation back pain, neck pain, spinal cord injury, phantom limb pain, carpal tunnel syndrome, multiple sclerosis, stroke, diabetic neuropathy and other metabolic conditions, herpes zoster infection, HIV-related neuropathies, nutritional deficiencies, toxins, immune-mediated disorders, physical trauma to a nerve trunk, mononeuropathy, polyneuropathy, nerve entrapment, cancer, chemotherapy, radiation injury, surgery, radiculopathy and scar pain.

Nociceptive pain may be found in conditions such as for example without limitation sprains, bone fractures, degenerative disease of discs and joints, back pain, neck pain, burns, bumps, bruises, inflammation for example from infection or arthritis, obstructions and myofascial pain.

In an embodiment of mixed pain, acute painful conditions, often associated with nociceptive pain, may transition to chronic neuropathic pain in a subject. Alternatively, a subject may have mixed pain including one or more condition associated with neuropathic pain and one or more condition associate with nociceptive pain. A subject with mixed pain may have back pain, neck pain, or both back pain and neck pain with neuropathic and nociceptive components. For example, without limitation, mixed pain may include back pain, neck pain, or both after surgery, e.g., postlaminectomy syndrome.

The present invention includes methods for treatment of pain, wherein pain in the subject is reduced or eliminated as compared with pain before treatment of the subject. Reduction of pain includes a reduction in pain by any amount and may be measured by any means conventionally used by the skilled artisan to evaluate pain in a subject. Elimination of pain in a subject means that no pain is detected in a subject as measured by conventional means or no pain is reported by the subject.

Effective treatment of pain in a subject may include any reduction of pain, including for example decreased burning, pricking, tingling, aching, throbbing, stinging, soreness or any combination thereof in the subject.

Methods of treatment of pain provided herein may include measuring reduction of pain by any conventional means known to the skilled artisan. For example, in some rodents, a tail flick study may be used to assess pain before and after administration of a mixture or composition of the invention. In an embodiment, for a human subject self-reporting may be used to identify decreased pain. Alternatively, functional magnetic resonance imaging (fMRI) may be used in a subject to identify decreased pain following administration of a mixture or composition of the present invention.

In accordance with the methods of the present invention, reduction or elimination of pain in a subject may last for any amount of time. For example, reduction or elimination of pain may last for about 1 hour, about 2 hours, about 3 hours, about 4 hours, about 5 hours, about 6 hours, about 7 hours, about 8 hours, about 10 hours, about 12 hours, about 14 hours, about 16 hours, about 20 hours, or about 24 hours. In other preferred embodiments reduction or elimination of pain in a subject may last for about 2 days, about 3 days, about 4 days, about 5 days, about 6 days, or about 7 days. In further preferred embodiments, reduction or elimination of pain in a subject may last for about 2 weeks, about 3 weeks, about a month, about 2 months, about 3 months, about 4 months, about 5 months, about 6 months, about 1 year, or for as long as the mixtures or compositions or the present invention continue to be administered. It is also contemplated that the mixtures and compositions of the present invention may be administered in an extended release formulation, such as a formulation that is suitable for dosing, for example without limitation, once a week, once every two weeks, or once a month.

The present mixtures and compositions show advantages as compared with other mixtures and compositions containing racemic methadone. These advantages include for example, reduced morbidity, mortality or both. Further, a mixture or composition of the present invention may reduce tolerance to and dependence upon morphine or other opioids. A mixture or composition of the present invention may reduce tolerance to and dependence upon L-methadone.

In a racemic methadone study by Morley, researchers used two doses, namely 10 mg and 20 mg of racemic methadone. In the study of non-racemic, 3:1 ratio of D:L methadone, a placebo-adjusted relief of average daily pain intensity 3 times better than 10 mg of racemic methadone and 54% better than 20 mg of racemic methadone was achieved. (See e.g., Example 4).

As such, there is a more than additive effect on neuropathic pain when D-methadone and L-methadone are administered in the ratios provided herein.

Non-racemic mixtures of the present invention also have unexpectedly fewer side effects in subjects. Such a result is both surprising and beneficial. For example, subjects treated with a non-racemic mixture or composition of the present invention may show fewer instances of nausea, vomiting, or nausea and vomiting. Subjects may continue treatment with non-racemic mixtures or compositions of the present invention when subjects taking an equal dosage of a single one of the isomers from the non-racemic mixture have discontinued treatment with that single isomer.

For example, unexpectedly better tolerance was also observed by administration of a 3:1 mixture of D-methadone to L-methadone than for administration of the racemic mixture in Morley. A 17% patient withdrawal rate was observed with administration of a 3:1 ratio of D-methadone to L-methadone vs. observation of a 37% patient withdrawal rate with administration of racemic methadone in Morley.

As such, non-racemic mixtures of D-methadone or pharmaceutically acceptable salt thereof to L-methadone or pharmaceutically acceptable salt thereof in the ratios described herein provide reduction of pain that is more than additive based on expected contribution of each isomer to pain reduction and provide reduced side effects. Such results are surprising and unexpected and may be highly beneficial.

Another advantage that may be found where a non-methadone opioid is included in the mixture or composition is, without limitation, control of neuropathic pain by a non-racemic methadone mixture and control of nociceptive pain by a non-methadone opioid. Alternatively or additionally, potentiation of morphine or codeine by L-methadone may be found.

The non-racemic mixtures of the present invention may also result in a decrease in tolerance, addiction, or tolerance and addiction of opioid drugs. In an embodiment, tolerance, addiction, or tolerance and addiction are decreased due to the surprising, more than additive effects of the non-racemic mixtures of the present invention.

EXAMPLES

Example 1

Preparation of 75%:25% by Weight D-Methadone:L-Methadone

A non-racemic mixture of methadone-HCl in a ratio of 3:1 by weight of D- and L-isomers was prepared.
75%:25% D-methadone:L-methadone, referred to by the following designations:

(IUPAC): Mixture of 75% (6S)-6-(dimethylamino)-4,4-dipheylhepan-3-one hydrochloride and 25% (6R)-6-(dimethylamino)-4,4-dipheylhepan-3-one hydrochloride.

Mixture of 75% (S)-(+)-methadone hydrochloride and 25% (R)-(−)-methadone hydrochloride.

Mixture of 75% (S)-6-dimethylamino-4,4-dipheylhepan-3-one hydrochloride and 25% (R)-6-dimethylamino-4,4-dipheylhepan-3-one hydrochloride.

Other Names, e.g. CAS registry: mixture of 75% 15284-15-8 and 25% 5967-73-7

Structural Characteristics of 75/25 D/L Methadone-HCl Included:

75% Molecular Formula: $C_{21}H_{27}NO \cdot HCl$

Relative Molecular Mass: 345.91

Chirality: 75/25 ratio of D and L isomers at C-6.

General Properties of 75/25 D/L Methadone-HCl Included the Following Physical Characteristics:

Solubility: Methadone HCl was readily soluble in water, alcohols and methylene chloride. It was practically insoluble in ether.

Appearance: 75/25 D/L-methadone HCl drug substance was a white solid.

Melting Point: 241° C.

Manufacturer(s) 75/25 D/L Methadone HCl:

Albany Molecular Research, Inc., Albany, N.Y. 12212

Description of Manufacturing Process and Process Controls 75/25 D/L Methadone HCl:

The process scheme for 75/25 D/L-methadone HCl used by the drug substance manufacturer is shown in Scheme 1.

Scheme 1- Resolution Process Scheme

Step 1: Formation of racemic methadone free base

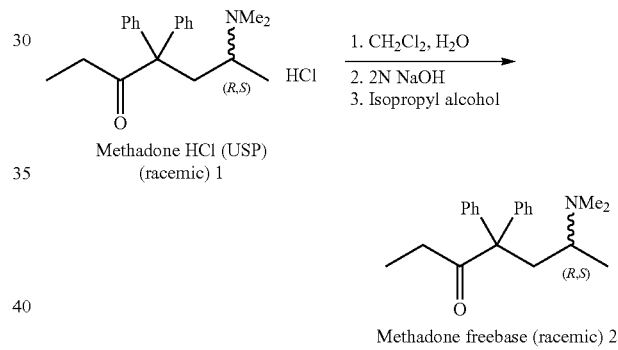

Methadone HCl (USP) (racemic) 1

Methadone freebase (racemic) 2

Step 2: Resolution of d-methadone

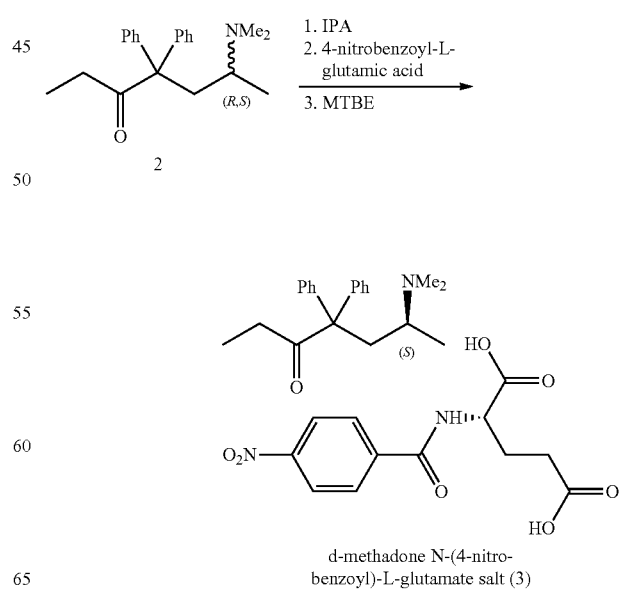

d-methadone N-(4-nitro-benzoyl)-L-glutamate salt (3)

Step 3: 75/25 d/l methadone free base

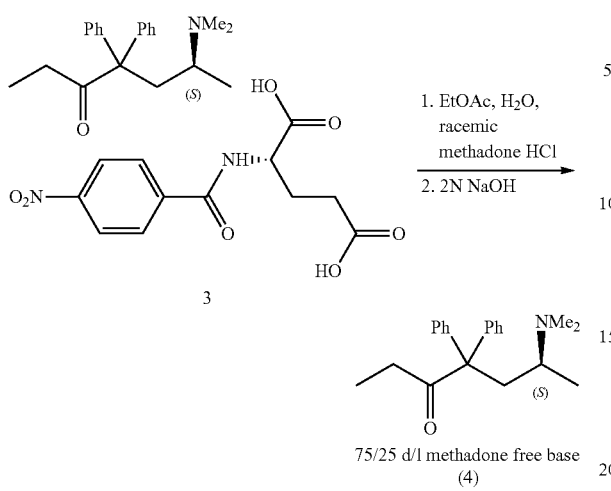

Step 4: Formation of 75/25 d/l methadone HCl

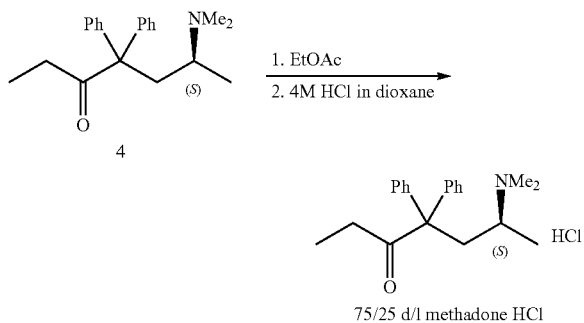

The process consisted of taking cGMP racemic methadone HCl (USP) and converting it to the desired 75/25 D/L isomer ratio. This was accomplished by resolution via diasteriomeric crystallization with 4-nitrobenzoyl-L-glutamic acid and adjustment to the correct ratio by adding back racemic methadone HCl. The process may be broken down into the following four steps:

Step 1: Racemic methadone HCl was free based in methylene chloride using an aqueous solution of 2N sodium hydroxide followed by solvent swap into isopropanol.

Step 2: The free base was converted to the N-(4-nitrobenzoyl)-L-glutamic acid salt and partial resolution (approximately 90:10 D/L methadone moiety) was obtained by crystallization from a mixture of isopropanol/tert-butyl methyl ether.

Step 3: The material enriched in the D isomer (>75%) was slurried in purified water and ethyl acetate with a calculated amount of racemic methadone HCl to obtain an isomer ratio of 75/25 of D/L. The free base was regenerated using 2N NaOH.

Step 4: The 75/25 D-/L-methadone free base was converted to the HCl salt and precipitated as the hydrochloride salt using 4 M HCl in dioxane.

Process Description:

The clinical trial lot of 75/25 D/L methadone HCl material was manufactured from 1000 g racemic methadone HCl. The process produced 508 g of 75/25 D/L-methadone HCl. The drug substance was produced using a 20-L glass-jacketed reactor, a 12-L glass-jacketed kettle. Solvents were removed using a 20-L rotary evaporator. The solids were isolated on a 10-inch table top HDPE Buchner funnel and dried inside a Hastelloy tray dryer. The following process description is based on this scale.

Step 1: Formation of Racemic Methadone Free Base Reaction:

Reaction:

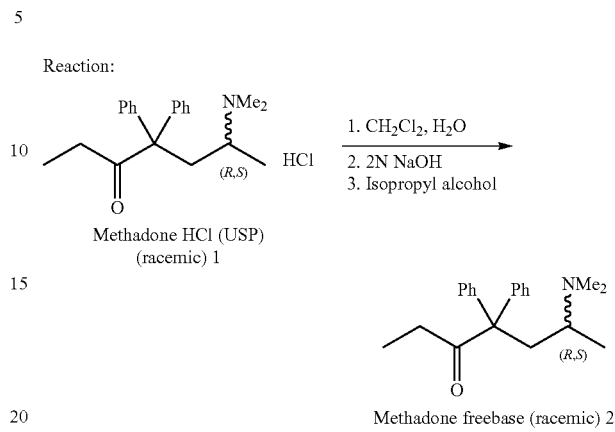

Racemic methadone HCl (1.0 kg), methylene chloride (6.6 kg), and purified water (5.0 kg) were charged to 20-L reactor. Temperature of the batch was adjusted to 15-25° C. 2 N sodium hydroxide solution (2.8 kg) was added, maintaining the batch temperature at less than 35° C. The batch was agitated for a minimum of 2 hours. The layers were allowed to separate. If the pH of the upper aqueous layer was less than 9.0, 2 N sodium hydroxide solution (0.5 kg) was added and the pH was rechecked. The lower organic layer containing the batch was transferred to a glass carboy. Methylene chloride (6.6 kg) was charged to the reactor as a back-extraction. Methylene chloride collections were combined. Purified water (5 kg) was charged to the organic collections in the reactor and agitated for 30 minutes. The phases were permitted to settle and the lower organic layer was retained. If the pH of the upper aqueous layer was ≥8.5, the purified water wash was repeated.

The batch was transferred in portions into a rotary evaporator and the batch was vacuum-distilled to 2-3 L at a batch temperature <30° C. Isopropanol (7.9 kg) was charged into the rotary evaporator and the batch vacuum-distilled to 2-3 L at a batch temperature <45° C. Isopropanol (3.3 kg) was charged to the batch and the batch transferred to the reactor.

Step 2: Resolution of D-Methadone

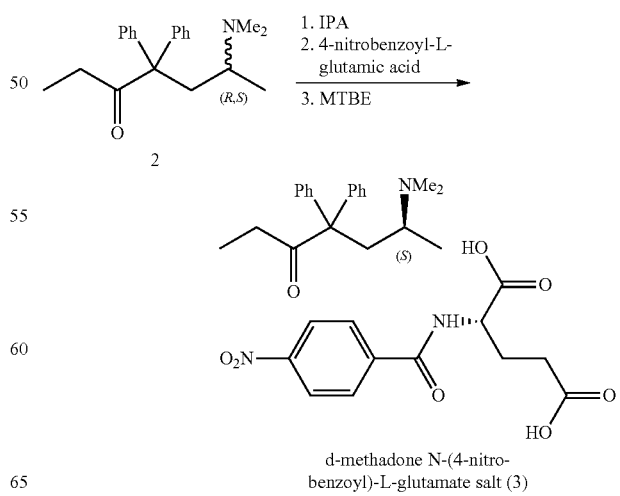

4-nitrobenzoylglutamic acid (0.44 kg, 0.5 equiv) was charged to the reactor. The batch was heated to reflux and agitated for 1-2 hours. The temperature was adjusted to 44-55° C. and tert-butyl methyl ether (6.1 kg) was charged to the reactor maintaining the batch temperature above 45° C. The batch temperature was adjusted to 15-25° C. at a rate of 10° C./hour. tert-butyl methyl ether (1.5 kg) was charged to the batch and agitated for 2 hours. It was verified that the batch had precipitated. The batch was transferred in portions into a rotary evaporator and the batch was vacuum-distilled to 2-3 L at a batch temperature <30° C. The batch was filtered on a table top Buchner funnel. The filter cake was washed twice with tert-butyl methyl ether (1.5 kg). The cake was conditioned for 30 minutes. The batch was transferred to drying trays, and the batch was dried to a constant weight in vacuum dryer at 30-40° C. The batch was transferred into a 4 L HDPE bottle and sample (IPC2-Methadone 4 Nitrobenzoyl Glutamate D/L ratio).

Step 3: 75/25 D/L-Methadone Free Base

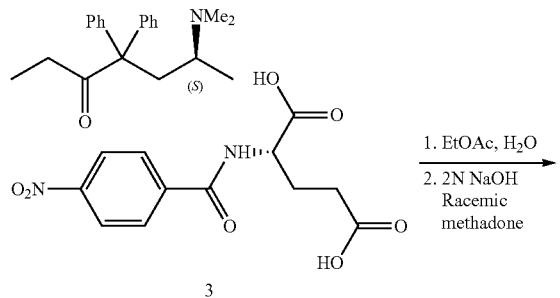

D-methadone 4-nitrobenzoyl glutamate (90% from 4 L HDPE bottle), racemic methadone HCl (calculated charge based on in-process measurement of isomer ratio after Step 2), ethyl acetate, and purified water was charged into the reactor and the batch temperature was adjusted to 15-25° C.

2 N sodium hydroxide solution (calculated charge based on D-methadone 4-nitrobenzoyl glutamate charge) was charged to the batch at less than 40° C. The batch was agitated until it went into solution. The phases were allowed to settle, and the pH of the lower aqueous layer was checked. If pH was ≤9.0, more 2 N sodium hydroxide solution was added to the batch and the pH rechecked. The batch was sampled for D/L ratio. If the D/L ratio was greater than 0.77, racemic methadone HCl was added to lower the ratio. If the D/L ratio was less than 0.73, D-methadone 4-nitrobenzoyl glutamate was added to raise the ratio. The lower aqueous layer was separated from the batch and discarded. The organic layer was rinsed with purified water and it was confirmed that the pH of the aqueous layer was ≤8.0.

Step 4: Formation of 75/25 D/L-Methadone HCl

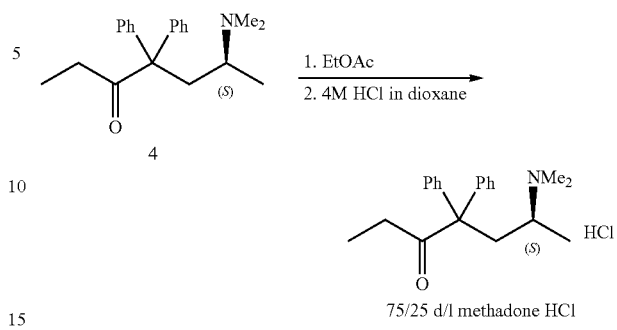

The batch was transferred from the reactor to the rotary evaporator in portions and vacuum-distilled to 1-2 L at a bath temperature <40° C. Ethyl acetate was charged to the batch and a sample tested for water content. If water was >1600 ppm, the batch was vacuum-distilled to 1-2 L at less than 40° C., ethyl acetate was charged, and the batch tested again for water content. The batch was transferred through a 1.2 micron in-line filter to the reactor and the batch temperature adjusted to 15-25° C. Dioxane in HCl was charged to the batch through a 1.2 micron in-line filter at a temperature below 30° C., and the batch was agitated for 2 hours. The organic layer was rinsed with purified water and it was confirmed that the pH of the aqueous layer was ≤8.0. The batch was transferred to a table top Buchner funnel and filtered. The cake was washed with ethyl acetate (0.9 kg) and conditioned for 30 minutes. The batch was transferred to two drying trays and vacuum-dried for 15 hours at 70-80° C. The batch was sampled to confirm that the lot met specifications for solvents and water content. The material was off-loaded, screened, sampled, and packaged.

Example 2

Dosing of Patients with Painful Diabetic Neuropathy

Potential patients were recruited by advertising and screened via interview, review of health history and medications, physical examination, lab work, and ECG. Potential patients with painful diabetic neuropathy for at least 6 months and a pain score greater than or equal to 4 were selected as patients. Potential patients were excluded if they met one or more of the following exclusion criteria: a pain diagnosis other than painful diabetic neuropathy, inadequate renal or kidney function, abnormal cognition, recent respiratory depression or sleep apnea, unstable cardiovascular disease, hypotension, ECG with an abnormal QT interval, pregnancy, recent history of drug or alcohol abuse (or positive test indicating either or both), use of strong opioids within the past 3 months, participation in one or more other research studies, or allergy to methadone.

Selected patients with painful diabetic neuropathy for at least 6 months and pain score greater than or equal to 4 were randomized to receive in double-blind, randomized, cross-over fashion capsules containing either 5 mg of drug (75:25 D:L-methadone) or 5 mg of placebo. Patients were subjected to forceful weekly titration of doses from 15 mg the first week, to 30 mg the second week, and to 40 mg the third and fourth weeks. After one week of washout period, patients previously taking a placebo were switched to the methadone dosage regimen and patients previously taking methadone were switched to a placebo.

The average daily pain score and the worst daily pain scores were measured. Patients recorded their pain score four times daily on a scale of 0 to 10. Additionally, pain scores were measured using a Visual Analog Scale (VAS) during weekly visits to the study center.

VAS is a measurement instrument that measures a characteristic or attitude that is believed to range across a continuum of values. For example, the amount of pain that a patient feels may range across a continuum from no pain to an extreme amount of pain. From the patient's perspective this spectrum appears continuous and does not take discrete jumps. In order to capture this underlying continuum, VAS was devised, and in the present study, VAS was used as described here. (See e.g., D. Gould et al., *J. Clin. Nursing*, 10: 697-706 (2001)).

VAS was conducted by using a horizontal line, 100 mm in length, anchored by word descriptors at each end, as illustrated below. Patients marked on a line (as shown below) the point that best represented their perception of pain.

How severe is your pain today? Place a vertical mark on the line below to indicate how bad you feel your pain is today.

No pain  Very severe pain

Effects of the interpersonal, technical and communication skills of the nurse on the effectiveness of treatment.

A VAS score was determined by measuring in millimeters from the left hand end of the line to the point that the patient marked.

Table 2a below shows significant advantages of 75:25 D/L-methadone vs. racemic methadone study results (see e.g., 15 mg results). This table shows statistically significant difference for our drug vs. placebo.

TABLE 2a

Changes in VAS Scores (SF-MPQ) and Between-Treatment Comparisons
Study Part 1
Primary Efficacy Population - Subjects who
completed all scheduled visits of the Study Part I

| Treatment Dose | Statistics | Methadone | Placebo | P-Value(1) |
|---|---|---|---|---|
| 15 mg | N | 19 | 19 | |
| | Mean | −12.8 | −2.8 | |
| | Std Dev | 15.3 | 16.8 | |
| | Median | −7.0 | −5.0 | |
| | Min; Max | −47.0; 5.0 | −48.0; 28.0 | |
| | | | | Difference in means (95% CI): −10.1 (−21.0; 0.9) 0.070 |
| 30 mg | N | 20 | 20 | |
| | Mean | −14.9 | −8.7 | |
| | Std Dev | 17.7 | 16.7 | |
| | Median | −8.0 | −8.0 | |
| | Min; Max | −48.0; 3.0 | −50.0; 28.0 | |
| | | | | Difference in means (95% CI): −6.3 (−17.4; 4.9) 0.255 |
| 15-30 mg (Combined)* | N | 39 | 39 | |
| | Mean | −13.9 | −5.8 | |
| | Std Dev | 16.4 | 16.8 | |
| | Median | −8.0 | −6.0 | |
| | Min; Max | −48.0; 5.0 | −50.0; 28.0 | |

TABLE 2a-continued

Changes in VAS Scores (SF-MPQ) and Between-Treatment Comparisons
Study Part 1
Primary Efficacy Population - Subjects who
completed all scheduled visits of the Study Part I

| Treatment Dose | Statistics | Methadone | Placebo | P-Value(1) |
|---|---|---|---|---|
| | | | | Difference in means (95% CI): −8.1 (−15.6; −0.6) 0.035 |
| 40 mg (1$^{st}$ Week) | N | 20 | 20 | |
| | Mean | −19.5 | −9.0 | |
| | Std Dev | 19.7 | 17.3 | |
| | Median | −13.0 | −6.5 | |
| | Min; Max | −67.0; 10.0 | −56.0; 18.0 | |
| | | | | Difference in means (95% CI): −10.5 (−19.6; −1.4) 0.026 |
| 40 mg (2$^{nd}$ Week) | N | 19 | 19 | |
| | Mean | −20.7 | −12.6 | |
| | Std Dev | 21.9 | 21.0 | |
| | Median | −10.0 | −9.0 | |
| | Min; Max | −68.0; 4.0 | −65.0; 17.0 | |
| | | | | Difference in means (95% CI): −8.1 (−18.3; 2.2) 0.116 |
| 40 mg (Both Weeks) | N | 39 | 39 | |
| | Mean | −20.1 | −10.7 | |
| | Std Dev | 20.5 | 19.0 | |
| | Median | −12.0 | −8.0 | |
| | Min; Max | −68.0; 10.0 | −65.0; 18.0 | |
| | | | | Difference in means (95% CI): −9.3 (−15.8; −2.8) 0.006 |

(1)VAS—Visual Analog Scale; SF-MPQ: Short Form McGill Pain Questionnaire,
(2) A paired t-test (two-sided) is used. Supporting p-values from the crossover analysis of variance model are provided in the Statistical Appendix.
*Combined refers to a pooling of results for patients who received 15 mg and 30 mg doses.

Example 3

In Vivo Study of 3:1 D:L Methadone

Table 3a below shows a statistically significant difference for 75:25 D:L-methadone vs. placebo.

TABLE 3a

Results: Study Part I - Primary Efficacy Analyses Statistically significant treatment differences for the first two planned primary endpoints -Differentiation from placebo at the lowest (15 mg/day) dose Changes in Average Daily Pain Scores and Between-Treatment Comparisons Primary Efficacy Population; Two Clinical Sites Combined

| Dose | Xxxxxxx ™ Mean (SD) | Placebo Mean (SD) | Difference in Means (95% CI) | P-value (paired t-test; two-sided) |
|---|---|---|---|---|
| 15 mg | −0.88 (1.46) | −0.04 (0.87) | −0.84 (−1.64; −0.04) | 0.041 |
| 30 mg | −1.41 (1.87) | −0.26 (1.17) | −1.14 (−2.30; 0.02) | 0.054 |
| 15-30 mg Combined | −1.14 (1.67) | −0.15 (1.02) | −0.99 (1.67; −0.31) | 0.005 |
| 40 mg (1$^{st}$ Week) | −1.57 (1.98) | −0.48 (1.15) | −1.08 (−2.20; 0.03) | 0.057 |
| 40 mg (2$^{nd}$ Week) | −1.73 (2.01) | −0.56 (1.22) | −1.17 (−2.28; −0.06) | 0.040 (Primary Endpoint) |
| 40 mg (Both Weeks) | −1.65 (1.97) | −0.52 (1.17) | −1.13 (−1.88; −0.38) | 0.004 (Primary Endpoint) |

Example 4

Comparison of In Vivo 3:1 D:L-Methadone Study Results with Racemic Methadone Study Results by Morley et al.

Racemic methadone previously showed efficacy in the treatment of neuropathic pain in a double-blind randomized controlled crossover study by Morley et al. (2003). Although Morley did not use forceful titration through 3 different doses, the study described in the preceding examples was organized similarly to that of Morley, with both studies providing a double-blind, randomized crossover with increasing dose. As such, the following comparisons of outcome were made.

It was expected that the results of the present study would show an arithmetic sum of effect based on each isomer.

In the Morley racemic methadone study, researchers used two doses, namely 10 mg and 20 mg of racemic methadone (or 5 mg/5 mg D-methadone/L-methadone and 10 mg/10 mg of D-methadone/L-methadone).

In the present study, the lowest tested dose was 3.75 mg D-methadone/11.25 mg L-methadone.

D-methadone was expected to have a more significant effect than L-methadone in treatment of neuropathic pain, and worse results were expected in the treatment of neuropathic pain when using 3.75 mg D-methadone/11.25 mg L-methadone as compared with the racemic methadone (containing 5 mg of each D-methadone and L-methadone) of Morley.

Moreover, even if L-methadone had been considered to be more significant in inhibition of neuropathic pain, at best, no better analgesia than 20 mg of racemic methadone (containing 10 mg each of D-methadone and L-methadone) was expected.

Unexpectedly, the 3 to 1 mixture of D- to L-methadone produced a placebo-adjusted relief of average daily pain intensity that was 3 times better than 10 mg of racemic methadone (−10.1 vs. −3.20) and 54% better than 20 mg of racemic methadone (−10.1 vs. −6.56).

These data suggest that there was a more than an additive effect on neuropathic pain when D-methadone and L-methadone were administered in a 3:1 ratio. Variation of the ratio by 2-3% produced comparable results.

Unexpectedly better tolerance of a 3:1 mixture of D-methadone to L-methadone was also observed. The number of patients who had to terminate the study because of side effects (mostly nausea and vomiting) was more than twice lower than in the Morley study of racemic methadone. 17% of patients withdrew from this study as compared with a 37% withdrawal rate in Morley. (17% vs. 37%).

Thus, non-racemic mixtures of D-methadone or pharmaceutically acceptable salt thereof to L-methadone or pharmaceutically acceptable salt thereof in the ratios described herein provide reduction of pain that is more than additive based on expected contribution of each isomer to pain reduction and provide reduced side effects. Such results were surprising and unexpected and may be highly beneficial.

While the present invention has been described by reference to various embodiments, the present invention is not in any way limited to the specifically disclosed embodiments. The present description is not intended to limit the present invention; to the contrary, various modifications will be apparent to those skilled in the art by reference to the description of the present invention. Such modifications, alternatives, and equivalents fall within the spirit and scope of the present invention.

What is claimed:

1. A pharmaceutical composition comprising a non-racemic mixture of D-methadone or pharmaceutically acceptable salt thereof and L-methadone or pharmaceutically acceptable salt thereof and a pharmaceutically acceptable carrier, wherein the D-methadone or pharmaceutically acceptable salt thereof and L-methadone or pharmaceutically acceptable salt thereof are present in a ratio of about 3:1.

2. The pharmaceutical composition according to claim 1, further comprising a pharmacologically effective amount of a non-methadone opioid.

3. The pharmaceutical composition according to claim 1, further comprising a partial opioid agonist.

4. The pharmaceutical composition according to claim 1, further comprising a non-opioid analgesic.

5. The pharmaceutical composition according to claim 1, further comprising a skeletal muscle relaxant.

6. The pharmaceutical composition according to claim 1, further comprising a nonbarbiturate sedative.

7. A method for treatment of neuropathic pain in a subject comprising administering the pharmaceutical composition of claim 1.

8. A pharmaceutical composition comprising a non-racemic mixture of D-methadone or pharmaceutically acceptable salt thereof and L-methadone or pharmaceutically acceptable salt thereof, at least one non-methadone opioid and a pharmaceutically acceptable carrier, wherein the D-methadone or pharmaceutically acceptable salt thereof and L-methadone or pharmaceutically acceptable salt thereof are present in a ratio of about 3:1.

9. A method for treatment of mixed pain in a subject comprising administering the pharmaceutical composition of claim 8.

\* \* \* \* \*